United States Patent [19]

Langeveld et al.

[11] Patent Number: 5,783,183
[45] Date of Patent: Jul. 21, 1998

[54] CLONING OF THE ZYMOCIN GENE AND USE OF ZYMOCIN IN BEVERAGES

[75] Inventors: Pieter Cornelis Langeveld, Delft; Pieter Van Solingen, Naaldwijk; Jacobus Stark, Rotterdam; Adrianus Wilhelmus Hermanus Vollebregt, Naaldwijk, all of Netherlands

[73] Assignee: Gist-brocades, B.V., Netherlands

[21] Appl. No.: 331,657

[22] PCT Filed: Mar. 3, 1994

[86] PCT No.: PCT/EP94/00634

§ 371 Date: Feb. 22, 1995

§ 102(e) Date: Feb. 22, 1995

[87] PCT Pub. No.: WO94/20620

PCT Pub. Date: Sep. 15, 1994

[30] Foreign Application Priority Data

Mar. 3, 1993 [EP] European Pat. Off. ............. 93200610
May 10, 1993 [EP] European Pat. Off. ............. 93201314

[51] Int. Cl.$^6$ .................. A61K 37/48; C12N 9/00
[52] U.S. Cl. ........................... 424/94.1; 435/183
[58] Field of Search .................. 426/8; 530/300, 530/350; 424/94.1; 435/183

[56] References Cited

U.S. PATENT DOCUMENTS 4,695,468  9/1987  Boston ........................... 426/8

OTHER PUBLICATIONS

Mohamed etal 1978 Sudan J. Fd. Sci Technol. 10:55–64.
La Roceo etal 1985 Food Technology 39(7):49–52.
Martin etal 1984 Microbios Letters 26:115–119.

Sellar et al., "Ocular Injuries Due to Exploding Bottles of Carbonated Drinks", BMJ (1991) 202:176–177.

Willhoft, "Victims of the Pop Bottle", New Scientist, 21 Aug. 1986, pp. 28–30.

Makower et al., "The Inheritance of a Killer Character in Yeast (*Saccharomyces cereviseae*)" (1963) Proc. 11th Int. Congr. Genet. I. 1202.

Young, (1987) in The Yeasts, Rose A.H. et al. Eds. Acad. Press, London. 2:131–164.

Nomoto et al., "Distribution of Killer Yeasts in the Genus Hansenula", *Agric. Biol. Chem.* 48:807–809 (1984).

Ashida et al., "New Killer Toxin of *Hansenula mrakii*", *Agric. Bio. Chem.* 47:2953–2955 (1983).

Yamamoto et al., "Application of Monoclonal Antibodies to the Isolation and Characterization of a Killer Toxin Secreted by *Hansenula mrakii*" (1986) FEBS 195:253–257.

Ohta et al., "Production, Purification and Characterization of HYI, an Anti-yeast Substance, Produced by *Hansenula saturnus*", *Agric. Biol. Chem.* 48:903–908 (1984).

*Primary Examiner*—Karen Carlson
*Attorney, Agent, or Firm*—Morrison & Foerster LLP

[57] ABSTRACT

The present invention discloses a method for the preservation of beverages comprising the use of a killer toxin. Specifically, zymocin is used in carbonated drinks. The zymocin is shown to be active against a wide range of different yeast strains. The invention further discloses a DNA fragment encoding zymocin. The DNA sequence is also disclosed.

8 Claims, 1 Drawing Sheet

TTAGCATGATTGCCTATTGGATCGGTGCTTCACAGTAATTGTTGTTCAAACTGATCAAGA

AGCACAAGGAAGGGTGCGCTCAATTGGTACTTTCGCAGCAAGATCAGGAAGCAGGTCGCA

GACTTCGACCACTTGCGGTCTCGAGAAGTTGTCAGCGAAGAAAGAAAACAGAGTTCAGCA

ACTTGTCGGATTAGGAAAACTGTATGCAATGCAATGCGCAAAAACGCTGTCTGATCACTG

GGTGTTTATCCATCAGAGAGTGAAGCACGCGGAGCTGCCACAAACCAACTTCGAAGATTT

TCGTTAGATGGGTATATAAAGACTTCCACTTCCCTGACAAGTCCCATACACTGTCTTCCC

ACATCTTTCCCCTTGAATCACGAAAAAAGTCAGGAACTTTTGTACTTGACATTTCCGCCC

AACATGAAATTTTCCTTCGTTTACGGTTTGACAGGCTTCTTAGCAGCAACCTCATCAGCT
    MetLysPheSerPheValTyrGlyLeuThrGlyPheLeuAlaAlaThrSerSerAla

TTGCCTTCCGAAATCTTATCAACTGGCTATGAAAGAAGTGCATTGGAGAAGCGTGGTGAT
LeuProSerGluIleLeuSerThrGlyTyrGluArgSerAlaLeuGluLysArgGlyAsp

GGATACCTGATTATGTGCAAAAACTGTGACCCAAACACGGGTAGCTGTGATTGGAAGCAG
GlyTyrLeuIleMetCysLysAsnCysAspProAsnThrGlySerCysAspTrpLysGln

AACTGGAATACTTGTGTAGGCATAGGAGCTAATGTCCACTGGATGGTTACAGGCGGCAGC
AsnTrpAsnThrCysValGlyIleGlyAlaAsnValHisTrpMetValThrGlyGlySer

ACTGATGGGAAGCAAGGGTGTGCTACAATCTGGGAAGGCTCAGGATGTGTGGGTAGATCA
ThrAspGlyLysGlnGlyCysAlaThrIleTrpGluGlySerGlyCysValGlyArgSer

ACCACAATGTGTTGTCCGGCCAATACTTGTTGCAACATCAACACAGGGTTCTACATTCGC
ThrThrMetCysCysProAlaAsnThrCysCysAsnIleAsnThrGlyPheTyrIleArg

TCTTACAGACGTGTGGAATAGGTGATTAACTATATCAACCGTAATGGAAAATTCGTGAAC
SerTyrArgArgValGluEnd

CGAAATTTCATTTTTGAGGATACCACACCAACTTGCGCTCAGATCCGTCACGTTATATAT

TTCTATAATTTACGCTTTAATAGGTGAATGTACTATGAAGGCCTCTTTAGAAATTTATAC

CTCTTTTGATTATAGTGGCACTATGATTATATAGTGCGTGTGATTGCTAGAGAAAATTTC

AGAAAACTTCCGTATCGTCTGCACTGACATTGCTCAAGCACCAAAAAAGCAGTCTCCTGA

TATGTCACTTAAGATCAAGAATAGATGTTTAGATGTAGCTAGTGTTTATCTGACAATAAA

AGGACTCCTAAGGTACAAACGGCTGAGAGGCAAAGACTTTGAGGAATTTTGCTCAAGATT

CTGTGATTCAGCCTTTACCAGCGACCTATCCATGCACGAAGTACTCTCTA

FIG. 1

CLONING OF THE ZYMOCIN GENE AND USE OF ZYMOCIN IN BEVERAGES

TECHNICAL FIELD

The present invention discloses a method for preserving beverages comprising the use of a killer toxin. Specifically an effective amount of a zymocin is used. The zymocin is particularly used in carbonated drinks. The invention also discloses the cloning of the *Williopsis mrakii* DNA and the DNA sequence encoding zymocin. This makes possible overexpression and large scale production of zymocin.

BACKGROUND OF THE INVENTION

Spoilage of food by yeasts is a well known problem in food industry. In some products yeasts are the main source of spoilage. Fruits belong to the natural habitat of yeasts. Therefore, it is not surprising that fruit derived products and fruit containing products are susceptible to contamination by yeasts. Examples are fruit pulp, fruit juice, fruit containing softdrinks and carbonated beverages, which sometimes contain high percentages of fruit juice. Spoilage of those products is even a major problem in industry. Softdrinks and carbonated beverages are to be considered as a very selective environment for the growth of yeasts. This environment has peculiar physical characteristics specifically low pH, low oxygen concentration and high sugar concentration. Furthermore storage is at low temperature. Yeasts have the ability to ferment the sugars introduced as such or those introduced with the fruits. Outgrowth of yeasts is responsible for off-flavours, there is loss of texture quality and gas is produced. The production of gas can cause swelling or even blowing up of the container. In the case of carbonated beverages bottled in glass this phenomenon has caused severe injuries. Sellar. P. W. and P. B. Johnston (BMJ (1991) 303 176–177)) describe how the seriousness of ocular injuries caused by exploding bottles has been underestimated. T. Willhoft (New Scientist (1986) 21 Aug., 28–30) also reports the popping bottle problem. The problem is due to carbon dioxide and although not specifically reported it is known that this gas is also produced by yeasts.

Yeast genera most frequently isolated from fruit and fruit products are Saccharomyces, Kluvveromyces, Zygosaccharomyces, Debaryomyces, Hansenula, Candida, Pichia and Torulopsis. The yeasts are introduced into the products with the ingredients such as the fruits. The yeasts also may grow on the surfaces of the production equipment.

In spite of good hygienic production methods and the use of preservatives like sorbate and benzoate spoilage of fruit products is still very common. Chemical preservatives like sorbic acid and benzoic acid pose their own problems. The concentration of these chemicals needed to prevent the outgrowth of some yeast species commonly detected in fruit derived products is very high. The concentration of benzoate and/or sorbate permitted in those products is too low to prevent outgrowth of these yeasts.

Killer toxins are inhibitory molecules produced by a wide range of yeasts. The inhibitory molecules are polypeptides or polypeptide containing molecules which kill sensitive yeast cells. Killer toxins were first observed in certain strains of the genus Saccharomyces (Makower M. et al. (1963) Proc. 11th Int. Congr. Genet. I, 1202). Today many different killer toxin-producing yeast species are known (Young T. W. (1987) in The Yeasts, Rose A. H. et al. Eds. Acad. Press, London. 2: 131–164). The majority of the killer toxins are not very stable and therefore not useful as a preservative. However, various Hansenula species make an exception to this rule and produce very heat- and pH-stable killer toxins (Nomoto, H. et al. (1984) Agric. Biol. Chem. 48 : 807–809).

For commercial use as an anti-yeast preservative it is preferred to employ a stable killer toxin with a broad spectrum anti-yeast activity.

An example of such a killer toxin is the killer toxin produced and secreted by *Hansenula mrakii* IFO 0895. The killer toxin of *Hansenula mrakii* IFO 0895 is very stable against heat and in a pH range of 4–11. A broad spectrum activity was demonstrated (Ashida S (1983) Agric. Biol. Chem. 47: 2953–2955). Further characterization showed that the killer toxin is a polypeptide with a molecular mass of 10721 Da. The molecule contains 88 amino acid residues. The amino acid sequence of this polypeptide has been published (Yamamoto T. et al. (1986) FEBS 195: 253–257). The name of this microorganism has in the meantime been changed to *Williopsis mrakii*.

Another example of a stable killer toxin is the killer toxin produced by *Hansenula saturnus*. This killer toxin shows a large similarity in activity spectrum and heat stability with the *Williopsis mrakii* killer toxin, hereinafter further indicated as zymocin. The *Hansenula saturnus* killer toxin is a small polypeptide with a molecular mass of 8500 Da and an isoelectric point of 5.8 (Ohta, T. et al. (1984) Agric. Biol. Chem. 48 : 903–908).

The potential use of killer toxins—especially the above mentioned killer toxin—as a preservative against yeast spoilage in several food products is described, in Japanese patent application JP 62-40272.

The use of a killer toxin for the prevention of outgrowth of yeasts in fruit containing carbonated beverages, which are to be considered as products that are very sensitive for spoilage by yeasts, has not been reported to date.

SUMMARY OF THE INVENTION

The present invention describes a method for the preservation of beverages comprising the use of a killer toxin. The killer toxin is used in carbonated and non-carbonated beverages. The zymocin is used as such or in combination with other preservation systems. The zymocin prevents the outgrowth of a wide range of yeast species in carbonated beverages, especially fruit containing beverages.

The present invention also discloses the DNA sequence encoding zymocin obtainable from *Williopsis mrakii*.

The invention further discloses a DNA fragment containing the gene encoding the said zymocin.

Another aspect of the invention discloses vectors and host strains for producing zymocin.

The present invention makes possible the cloning, overexpression and large scale production of zymocins.

BRIEF DESCRIPTION OF THE FIGURES

FIG. 1 shows the partial nucleotide sequence (SEQ ID NO:1) of a 5 kb PstI fragment of *Williopsis mrakii* DNA containing the zymocin gene and the amino acid sequence (SEQ ID NO:2) of the coding region.

DETAILED DESCRIPTION OF THE INVENTION

The present invention describes the use of killer toxins. The killer toxins can be used as such they can also be used in combination with other preservation systems. Killer toxins can also be used together with other killer toxins. They asure the prevention of outgrowth of a wide range of yeast species in carbonated beverages, especially fruit containing beverages. In general the yeasts or other species are introduced in the drinks together with the fruits. It is also possible that the contamination occurs during the processing of the fluids or the fruits. The invention is therefore not restricted to beverages containing fruit material.

The killer toxins of the present invention are obtainable for *Williopsis mrakii*. They are characterized by their high pH- and thermal stability. Similar killer toxins also suitable in the uses claimed in the present invention are obtainable from *Hansenula saturnus*. Collectively these killer toxins are indicated as zymocins.

It is shown that the zymocins of the present invention are active against yeasts in carbonated beverages, both alcoholic- and non-alcoholic. Specifically, the zymocins are active in BRON ORANGE™, JAFFA DRINK™, 7-UP™, CERISE™ and STENDER BIER™. It is also demonstrated that the zymocins are active in fruit juices such as apple juice, orange juice and pear juice and black currant drink.

As representatives of yeasts of which the outgrowth can be controlled Saccharomyces and Zycosaccharomyces were used.

It is further shown that the killer toxins of the present invention is active against a wide range of yeasts and fungi. Activity is shown against *Brettanomyces anomalus, Brettanomyces intermedius, Candida glabrata, Debaryomyces hansenii, Dekkera anomala, Dekkera naardenensis, Hansenula arabitolgenus, Hanseniaspora uvarum, Pichia anomala, Pichia angusta, Pichia kluvveri, Saccharomyces cerevisiae, Saccharomyces exiguus, Williopsis saturnus, Zygosaccharomyces bailii, Zygosaccharomyces microellipsoides, Zygosaccharomyces rouxii, Candida boidinii, Candida etchellsii, Hanseniaspora osmophila, Pichia membraneafaciens, Rhodotorula mucilaginosa* and *Schizosaccharomyces pombe*

The invention further discloses a DNA fragment containing the gene encoding zymocin. The DNA is isolated using standard procedures.

The present invention also discloses the DNA sequence encoding zymocin obtainable from *Williopsis mrakii*. It is understood that these sequences can be used to device probes suitable for the identification of zymocin encoding genes from other Hansenula and Williopsis species. After identification the detected genes can be cloned and used for protein production as examplified herein by the *Williopsis mrakii* gene.

The sequence encoding the zymocins from other species can be cloned in suitable expression systems as shown in the examples for the *Williopsis mrakii* gene.

Furthermore cloning and expression vectors and host species for obtaining zymocin are disclosed.

The present invention makes possible the cloning, overexpression and large scale production of zymocin.

The zymocin can thus be obtained in large amounts and with a high purity. The zymocin gene can be cloned in suitable expression vectors. The choice of such vectors is dependent on the host organism. The host organism is preferably chosen from among species which are not susceptible to the activity of the zymocin. Examples of such organisms are Bacilli and Aspergilli. Preferred species are *Bacillus subtilis, Bacillus licheniformis, Bacillus alkaligenes, Bacillus amyloliquefaciens, Bacillus lentus* and *Bacillus stearothermophilus*. Preferred Aspergilli are *Aspergillus niger* and *Aspergillus nidulans*.

For the majority of species indicated cloning and expression vectors are known in the art and can be used for zymocin.

This method for preparing the zymocin is especially advantages since it is known that the *Williopsis mrakii* produces other killer toxines as well. By heterologous cloning and expression of the zymocin this source of contamination is avoided.

The zymocin can be used without extensive purification either in the presence or in the absence of the production host. Alternatively the zymocin can be purified, methods are known in the art. In the present examples FPLC is used, HPLC is another possibility. If zymocin is to be produced on a large scale different chromatographic methods are available, including ion-exchange chromatography and gel filtration.

EXAMPLE 1

Isolation of Zymocin from Williopsis

Strains

*Williopsis mrakii* IFO 895, *Hansenula saturnus* IFO 117 and *Hansenula saturnus* IFO 1466 were used as the zymocin producers. *Hansenula anomala* IFO 569 was used as a sensitive tester strain. Both strains were obtained from the Institute for Fermentation, Osaka, Japan. All other strains were obtained from the Centraalbureau voor Schimmelcultures (CBS), Baarn, The Netherlands.

Media

YEPD-broth consisted of Bacto-yeast extract (Difco) 1%, Bacto-peptone (Difco) 2% and glucose 2% in 50 mM citrate-phosphate buffer (pH 4.8). The complex medium was used to prepare seed cultures. Bacto-yeast nitrogen base (YNB) 1%, glucose 10% in 50 mM citrate-phosphate buffer (pH 4.4) was used as minimal production medium in shake flask fermentations.

Detection of the Activity

Serial dilutions (1:1) of the culture broth were made in microtiter plates. To each well an equal volume (100 µl) of a suspension of *Hansenula anomala* IFO 569 ($2.10^4$–$2.10^5$ cells per ml) was pipetted. The plates were incubated for 3 days at 25° C. The minimal concentration of zymocin, that inhibited the growth (MIC) of *Hansenula anomala* IFO 569 under these conditions, was defined to contain 1 arbitrary unit (AU) per ml.

To determine the Minimal Lethal Concentration (MLC) of zymocin, 5 µl from each well was spotted on YEPD, 2% agar plates. The plates were incubated for 2 days at 25° C.

Production

Small scale fermentations (100 ml) were carried out with *Hansenula mrakii* IFO 895 and both *Hansenula saturnus* strains, in 500 ml shake flasks with baffles. The flasks were incubated in an Incubator Shaker (New Brunswick Scientific, Edison, N.J., USA), at 250 r.p.m. at 25° C. for 72 hours.

Large scale fermentations were carried out in a 10 liter fermentor unit (L. Eschweiler & Co., Kiel, Germany). Four liter of YNB 2.5%, glucose 2.5% was inoculated with 1 liter of an overnight culture of *Williopsis mrakii* IFO 895 in YNB 1%, glucose 2.5%. After a batch phase of 15 hours a glucose solution (27.5%) was fed to the culture (100 gram per hour) for another 34 hours. The pH was kept at pH 5.0 using 4N NaOH/4N $H_2SO_4$, the temperature was kept at 25° C. The stirring rate was 300 rpm.

Purification

Cells were harvested by centrifugation. The filtrate was filter sterilized and the zymocin was precipitates by addition of 2 volumes of methanol. The precipitate was collected by filtration over sintered stainless steel and dried under vacuum at room temperature. The precipitate was dissolved (1.7%) in 10 mM phosphate buffer (pH 3.4) and loaded on S Sepharose Fast Flow HR 16/9.4 using a BioPilot FPLC unit (Pharmacia LKB, Uppsala, Sweden). Zymocin was eluted with 1M NaCl in 10 mM phosphate buffer (pH 3.4). The fractions, that contained zymocin activity were pooled, dialysed against 10 mM phosphate buffer (pH 4.4) and stored frozen at −20° C.

Characterization of Zymocin

Stability of Zymocin at Different pH Values

Fermentation broth of *Williopsis mrakii* with a zymocin activity between 64 and 128 AU/ml and of both *Hansenula saturnus* strains (32–64 AU/ml), was adjusted to various pH values using either 1M $H_3PO_4$ or NaOH. After stirring for 1 hour on a magnetic stirring device at room temperature, the solution was neutralized and the zymocin activity was determined. The results are presented in Table 1.

TABLE 1

| | Zymocin activity (AU/ml) | | |
|---|---|---|---|
| | *Williopsis mrakii* | *Hansenula saturnus* | |
| pH | IFO 895 | IFO 117 | IFO 1466 |
| 1 | 32–64 | n.d. | n.d. |
| 2 | 64–128 | n.d. | n.d. |
| 3–9 | 64–128 | 32–64 | 32–64 |
| 10 | 64–128 | n.d. | n.d. |
| 11 | 64–128 | n.d. | n.d. |
| 12 | 16–32 | n.d. | n.d. | n.d. not detected

Stability of Zymocin at High Temperatures

Fermentation broth of *Williopsis mrakii* (64–128 AU zymocin/ml) and of both *Hansenula saturnus* strains (32–64 AU/ml) was heated for 10 minutes at 80°, 100° and 120° C., respectively. The samples were cooled to room temperature and the zymocin activity was measured. The results are shown in Table 2.

TABLE 2

| | Zymocin activity (AU/ml) | | |
|---|---|---|---|
| | *Williopsis mrakii* | *Hansenula saturnus* | |
| Temperature | IFO 895 | IFO 117 | IFO 1466 |
| 25° C. | 64–128 | 32–64 | 32–64 |
| 80° C. | 64–128 | 32–64 | 32–64 |
| 100° C. | 64–128 | 16–32 | 16–32 |
| 120° C. | 16–32 | 8–16 | 4–8 |

EXAMPLE 2

Activity of Zymocin Against Various Yeast Strains

Twenty-six strains of various yeast species were used as indicator organism in the activity tests described in example 1. The MIC and MLC-values are given in Table 3.

TABLE 3

| | | *Williopsis mrakii* | | *Hansenula saturnus* | | | |
|---|---|---|---|---|---|---|---|
| | | IFO 895 | | IFO 117 | | IFO 1466 | |
| Species | Strain CBS No. | MIC (AU/ml) | MLC (AU/ml) | MIC (AU/ml) | MLC (AU/ml) | MIC (AU/ml) | MLC (AU/ml) |
| *Brettanomyces anomalus* | 77 | 64 | 128 | >512 | >512 | 1024 | 1024 |
| *Brettanomyces intermedius* | 1940 | 16 | 16 | >512 | >512 | 64 | 1024 |
| *Candida glabrata* | 2663 | 4 | 4 | 2 | 4 | 1 | 2 |
| *Debaryomyces hansenii* | 4373 | 128 | 256 | >512 | >512 | >1024 | >1024 |
| *Dekkera anomala* | 8138 | 64 | 128 | 8 | 8 | 4 | 4 |
| *Dekkera naardenensis* | 6115 | 16 | 32 | n.d. | n.d. | n.d. | n.d. |
| *Dekkera naardenensis* | 6041 | 4 | 8 | >512 | >512 | 1024 | 1024 |
| *Hansenula arabitolgenus* | 7164 | 8 | 16 | n.d. | n.d. | n.d. | n.d. |
| *Hanseniaspora uvarum* | 5934 | 1024 | 1024 | n.d. | n.d. | n.d. | n.d. |
| *Pichia anomala* | 1683 | 16 | 16 | 16 | 16 | 8 | 8 |
| *Pichia angusta* | 1976 | 128 | 1024 | n.d. | n.d. | n.d. | n.d. |
| *Pichia kluyveri* | 6859 | 4 | 4 | 4 | 8 | 4 | 4 |
| *Saccharomyces cerevisiae* | 425 | 256 | 512 | >512 | >512 | 512 | 512 |
| *Saccharomyces cerevisiae* | 1552 | 32 | 64 | 16 | 32 | 16 | 16 |
| *Williopsis saturnus* | 7192 | >1024 | >1024 | n.d. | n.d. | n.d. | n.d. |
| *Zygosaccharomyces bailii* | 1097 | 16 | 16 | 256 | 256 | 8 | 8 |
| *Zygosaccharomyces microellipsoides* | 427 | 16 | 32 | 32 | 32 | 16 | 16 |
| *Zygosaccharomyces rouxii* | 711 | 512 | 1024 | 256 | 256 | 256 | 256 |
| *Zygosaccharomyces rouxii* | 4564 | 256 | 512 | n.d. | n.d. | n.d. | n.d. |
| *Candida boidinii* | 6368 | inhibited | inhibited | n.d. | n.d. | n.d. | n.d. |
| *Candida etchelsii* | 2987 | inhibited | inhibited | n.d. | n.d. | n.d. | n.d. |
| *Hanseniaspora osmophila* | 4266 | inhibited | inhibited | n.d. | n.d. | n.d. | n.d. |
| *Pichia membraneafaciens* | 5756 | inhibited | inhibited | n.d. | n.d. | n.d. | n.d. |
| *Rhodotorula mucilaginosa* | 334 | inhibited | inhibited | n.d. | n.d. | n.d. | n.d. |
| *Schizosaccharomyces pombe* | 1042 | inhibited | inhibited | n.d. | n.d. | n.d. | n.d. |

EXAMPLE 3

Activity of Zymocin Against Yeasts in Carbonated Beverages

Two yeast strains: *Saccharomyces cerevisiae* CBS 425 and *Zygosaccharomyces rouxii* CBS 711, were grown in YEPD as described in Example 1. Suspensions ($2.10^5$ cells/ml) were made in various carbonated beverages. The same beverages were used to make serial dilutions (1:1) of zymocin (2048–2 AU/ml). Aliquot of 100 μg of the zymocin solution were brought into the wells of a microtiter plate. An equal volume of the yeast suspension in the carbonated beverages was pipetted into the wells and the MIC and MLC values were determined as described in Example 1. The results are shown in Table 4. The zymocin shows a high activity especially against *S. cerevisiae*.

TABLE 4

|  | *S. cerevisiae* CBS 425 | | *Z. rouxii* CBS 711 | |
| --- | --- | --- | --- | --- |
| Product | MIC (AU/ml) | MLC (AU/ml) | MIC (AU/ml) | MLC (AU/ml) |
| Apple-juice | 128 | 256 | 128 | 256 |
| Pear-juice | 128 | 256 | 128 | 256 |
| Orange-juice I | 256 | 512 | 128 | 256 |
| Orange-juice II | 128 | n.d. | 128 | n.d. |
| Grape-juice | >512 | >512 | 512 | 512 |
| Vegetable-juice | 512 | 1024 | 256 | >1024 |
| Bron Orange* | 16 | 16 | 256 | 256 |
| Jaffa Drink* | 16 | 16 | 128 | 128 |
| Stender B-ier** | 16 | 16 | 64 | 64 |
| Control: YEPD | 256 | 256 | 512 | 1024 |

*Carbonated lemonades
**Non-alcoholic beer
n.d. Not detected
Bron Orange ™, Jaffa Drink ™ and Stender Bier ™ are Trademarks.

EXAMPLE 4

Activity of Zymocin Against *Zygosaccharomyces bailli* in Black Currant Drink

Zymocin is tested in black currant drink. *Zygosaccharomyces bailii* CBS 1097 was grown for 24 hours at 30° C. in 25 ml BHI medium in a 100 ml shake flasks at 250 rpm in a shaking incubator (New Brunswick Scientific, Edison, N.J., USA). Serial dilutions of Zymocin in 25 ml black currant drink were made (0 to 250 AU/ml) and pipetted in 100 ml erlenmeyers. The Zymocin solutions were inoculated with the test strain in a concentration of $10^3$ cells per ml. The flasks were incubated at 30° C. After 1 day, the number of viable cells was determined by total plate counting on YEPD-agar.

TABLE 5

| Zymocin conc. (U/ml) | Number of viable cells/ml |
| --- | --- |
| 0 | >100.000 |
| 10 | 6000 |
| 50 | 3015 |

TABLE 5-continued

| Zymocin conc. (U/ml) | Number of viable cells/ml |
| --- | --- |
| 125 | 1770 |
| 250 | 1040 |

EXAMPLE 5

Activity of Various Zymocin Against Yeasts Strains in Non-alcoholic Beer

Four yeast strains: *Saccharomyces cerevisiae* CBS 425, *Saccharomyces cerevisiae* CBS 1552, *Saccharomyces exiguus* CBS 6946 and *Zygosaccharomyces bailii* CBS 1097 were tested for their sensitivity to variuos zymocins in non-alcoholic beer. The MIC and MLC values were determined the results are presented in Table 6.

| | Zymocin activity (AU/ml) | | | | | |
| --- | --- | --- | --- | --- | --- | --- |
| | *W. mrakii* | | *Hansenula saturnus* | | | |
| | IFO 895 | | IFO 117 | | IFO 1466 | |
| Strains | MIC | MLC | MIC | MLC | MIC | MLC |
| *S. cerevisiae* CBS 425 | 8 | 16 | 32 | 64 | 16 | 22 |
| *S. cerevisiae* CBS 1552 | 2 | 4 | 8 | 8 | 4 | 8 |
| *S. exiguus* CBS 6946 | 8 | 8 | 8 | 8 | 8 | 8 |
| *Z. bailii* CBS 1097 | 1 | 1 | 4 | 4 | 0.5 | 0.5 |

EXAMPLE 6

Activity of Various Zymocins Against Yeasts in Cerise™ and 7-Up™

Two yeast strains: *Zygosaccharomyces bailii* CBS 1097 and *Saccharomyces exiguus* CBS 6946 were grown in Cerise™ and 7-Up™, respectively. The MIC values were determined as described in Example 3. The results are presented in Table 7.

TABLE 7

| | | Zymocin activity (AU/ml) | | |
| --- | --- | --- | --- | --- |
| | | *W. mrakii* | *Hansenula saturnus* | |
| Drink | Strain | IFO 895 MIC | IFO 117 MIC | IFO 1466 MIC |
| Cerise ™ | *Z. bailii* CBS 1097 | 256 | 256 | 256 |
| 7-Up ™ | *S. exiguus* CBS 6946 | 128 | 128 | 128 |

EXAMPLE 7

Cloning of the Zymocin Gene of *Williopsis mrakii*

The amino acid sequence of *Williopsis mrakii* Zymocin is published earlier by Yamamoto, T., FEBS Letters 195 (1986), 253–257. Using these data a set of degenerated oligonucleotides was derived which coded for a chosen string of amino acids. The following oligonucleotides were synthesized:

```
         7     8     9    10    11    12
5'-    Met   Cys   Lys   Asn   Cys   Asp - 3'    (Seq. ID No: 1 and Seq ID No: 2)
       ATG   TGT   AAA   AAT   TGT   GAT
                C    G     C     C
        80    79    78    77    76    75    74    73
5'-    Tyr   Phe   GLy   Thr   Asn   Ile   Asn   Cys - 3'  (Seq. ID
                                                            No: 3 and 4)
       ATA   AAA   ACC   AGT   ATT   AAT   ATT   ACA
        G     G     T     T     G     T     G     G
                    C     C           G
                    G     G
```

A PCR experiment was carried out using the given oligo nucleotides as primers and chromosomal DNA of *Williopsis mrakii* IFO 895 as a template. In doing the PCR experiment a DNA fragment from *Williopsis mrakii* was amplified, with a length of 222 bp as expected. This fragment was used as a hybridization probe for a Southern blots of chromosomal *Williopsis mrakii* DNA, digested with various restriction enzymes. Positive hybridization signals were found with a Pst I fragments of 5 kb. Subsequently Pst I digested chromosomal DNA of *Williopsis mrakii* was separated by agarose gel electrophoresis on preparative scale. Fragments of 5±0.5 kb were isolated from the gel and ligated with the commercial available cloning vector pUC18 (Appligene, Strassbourg, France). The ligation mixtures were transformed to *Escherichia coli* XL1-Blue (Stratagene, La Jolla, Calif., USA). The 222 bp PCR fragment was used as a probe in a colony hybridization experiment to select for clones giving a positive hybridization signal. Two types of transformants were obtained, carrying pUC18 derived plasmids with the same 5 kb PstI fragment in 2 different orientations. The plasmids were called pUC18K1 and PUC18K2.

A part of the 5 kb fragment was sequenced using the oligo nucleotides mentioned above. The nucleotide sequence was translated in 3 different reading frames. One of these reading frames showed an amino acid sequence that contained the identical sequence of 88 amino acid, published before. Therefore we conclude we cloned the gene coding for the zymocin of *Williopsis mrakii*. The nucleotide sequence and the derived amino acid sequence of the zymocin gene is shown in FIG. 1 (Seq. ID No: 5 and 6)

We claim:

1. A method for preserving non-alcoholic, non-carbonated beverages comprising adding an effective amount of a yeast zymocin to said beverage.

2. A method according to claim 1 wherein said non-carbonated beverage contains fruit, fruit juice or a fruit extract.

3. A method according to claim 2 wherein the beverage is selected from the group consisting of apple juice, orange juice, pear juice and black currant drink.

4. A method according to claim 1 wherein said zymocin is obtainable from a yeast strain selected from a genus consisting of Hansenula and Williopsis.

5. A method according to claim 1 wherein said zymocin is added to achieve a final concentration of 128 to 512 AU/ml.

6. A method according to claim 5 wherein said zymocin is produced from an organism that has been altered to contain a DNA molecule that encodes said zymocin.

7. A method according to claim 6 wherein said DNA molecule encodes a zymocin having the amino acid sequence depicted in Sequence ID No:5.

8. A non-alcoholic, non-carbonated beverage having been preserved by the method of claim 5.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Williopsis mrakii
        ( B ) STRAIN: IFO 895

( v i i ) IMMEDIATE SOURCE:
        ( B ) CLONE: peptide1

( x i ) SEQUENCE DESCRIPTION: SEQ ID NO:1:

Met   Cys   Leu   Asn   Cys   Asp
        1                                5

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Williopsis mrakii
            ( B ) STRAIN: IFO 895

( v i i ) IMMEDIATE SOURCE:
            ( B ) CLONE: oligo1

( x i ) SEQUENCE DESCRIPTION: SEQ ID NO:2:

ATGTGYAARA AYTGYGAT                                                                         1 8

( 2 ) INFORMATION FOR SEQ ID NO:3:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
            ( A ) ORGANISM: Williopsis mrakii
            ( B ) STRAIN: IFO 895

( v i i ) IMMEDIATE SOURCE:
            ( B ) CLONE: peptide2

( x i ) SEQUENCE DESCRIPTION: SEQ ID NO:3:

Tyr  Phe  Gly  Thr  Asn  Ile  Asn  Cys
        1                   5

( 2 ) INFORMATION FOR SEQ ID NO:4:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
            ( A ) ORGANISM: Williopsis mrakii
            ( B ) STRAIN: IFO 895

( v i i ) IMMEDIATE SOURCE:
            ( B ) CLONE: oligo2

( x i ) SEQUENCE DESCRIPTION: SEQ ID NO:4:

RTARAANCCN GTRTTDATRT TRCA                                                                  2 4

( 2 ) INFORMATION FOR SEQ ID NO:5:

( i ) SEQUENCE CHARACTERISTICS:
            ( A ) LENGTH: 1250 base pairs
            ( B ) TYPE: nucleic acid
            ( C ) STRANDEDNESS: double (  D  ) TOPOLOGY: linear (  i i  ) MOLECULE TYPE: DNA (genomic)

(  i i i  ) HYPOTHETICAL: NO (  i v  ) ANTI-SENSE: NO (  v i  ) ORIGINAL SOURCE:
    (  A  ) ORGANISM: Williopsis mrakii
    (  B  ) STRAIN: IFO 895

(  i x  ) FEATURE:
    (  A  ) NAME/KEY: CDS
    (  B  ) LOCATION: 424..801
    (  D  ) OTHER INFORMATION: /codon_start= 424
                                / product= "Zymocin"

(  x i  ) SEQUENCE DESCRIPTION: SEQ ID NO:5:

```
TTAGCATGAT TGCCTATTGG ATCGGTGCTT CACAGTAATT GTTGTTCAAA CTGATCAAGA         60

AGCACAAGGA AGGGTGCGCT CAATTGGTAC TTTCGCAGCA AGATCAGGAA GCAGGTCGCA        120

GACTTCGACC ACTTGCGGTC TCGAGAAGTT GTCAGCGAAG AAAGAAAACA GAGTTCAGCA        180

ACTTGTCGGA TTAGGAAAAC TGTATGCAAT GCAATGCGCA AAACGCTGT CTGATCACTG         240

GGTGTTTATC CATCAGAGAG TGAAGCACGC GGAGCTGCCA CAAACCAACT TCGAAGATTT        300

TCGTTAGATG GGTATATAAA GACTTCCACT TCCCTGACAA GTCCCATACA CTGTCTTCCC        360

ACATCTTTCC CCTTGAATCA CGAAAAAAGT CAGGAACTTT TGTACTTGAC ATTTCCGCCC        420
```

| AAC | ATG | AAA | TTT | TCC | TTC | GTT | TAC | GGT | TTG | ACA | GGC | TTC | TTA | GCA | GCA | 468 |
|---|---|---|---|---|---|---|---|---|---|---|---|---|---|---|---|---|
|   | Met | Lys | Phe | Ser | Phe | Val | Tyr | Gly | Leu | Thr | Gly | Phe | Leu | Ala | Ala |   |
|   | 1 |   |   |   | 5 |   |   |   |   | 10 |   |   |   |   | 15 |   |

| ACC | TCA | TCA | GCT | TTG | CCT | TCC | GAA | ATC | TTA | TCA | ACT | GGC | TAT | GAA | AGA | 516 |
|---|---|---|---|---|---|---|---|---|---|---|---|---|---|---|---|---|
| Thr | Ser | Ser | Ala | Leu | Pro | Ser | Glu | Ile | Leu | Ser | Thr | Gly | Tyr | Glu | Arg |   |
|   |   |   |   | 20 |   |   |   |   | 25 |   |   |   |   | 30 |   |   |

| AGT | GCA | TTG | GAG | AAG | CGT | GGT | GAT | GGA | TAC | CTG | ATT | ATG | TGC | AAA | AAC | 564 |
|---|---|---|---|---|---|---|---|---|---|---|---|---|---|---|---|---|
| Ser | Ala | Leu | Glu | Lys | Arg | Gly | Asp | Gly | Tyr | Leu | Ile | Met | Cys | Lys | Asn |   |
|   |   |   | 35 |   |   |   |   | 40 |   |   |   |   | 45 |   |   |   |

| TGT | GAC | CCA | AAC | ACG | GGT | AGC | TGT | GAT | TGG | AAG | CAG | AAC | TGG | AAT | ACT | 612 |
|---|---|---|---|---|---|---|---|---|---|---|---|---|---|---|---|---|
| Cys | Asp | Pro | Asn | Thr | Gly | Ser | Cys | Asp | Trp | Lys | Gln | Asn | Trp | Asn | Thr |   |
|   |   | 50 |   |   |   |   | 55 |   |   |   |   | 60 |   |   |   |   |

| TGT | GTA | GGC | ATA | GGA | GCT | AAT | GTC | CAC | TGG | ATG | GTT | ACA | GGC | GGC | AGC | 660 |
|---|---|---|---|---|---|---|---|---|---|---|---|---|---|---|---|---|
| Cys | Val | Gly | Ile | Gly | Ala | Asn | Val | His | Trp | Met | Val | Thr | Gly | Gly | Ser |   |
|   | 65 |   |   |   |   | 70 |   |   |   |   | 75 |   |   |   |   |   |

| ACT | GAT | GGG | AAG | CAA | GGG | TGT | GCT | ACA | ATC | TGG | GAA | GGC | TCA | GGA | TGT | 708 |
|---|---|---|---|---|---|---|---|---|---|---|---|---|---|---|---|---|
| Thr | Asp | Gly | Lys | Gln | Gly | Cys | Ala | Thr | Ile | Trp | Glu | Gly | Ser | Gly | Cys |   |
| 80 |   |   |   |   | 85 |   |   |   |   | 90 |   |   |   |   | 95 |   |

| GTG | GGT | AGA | TCA | ACC | ACA | ATG | TGT | TGT | CCG | GCC | AAT | ACT | TGT | TGC | AAC | 756 |
|---|---|---|---|---|---|---|---|---|---|---|---|---|---|---|---|---|
| Val | Gly | Arg | Ser | Thr | Thr | Met | Cys | Cys | Pro | Ala | Asn | Thr | Cys | Cys | Asn |   |
|   |   |   |   | 100 |   |   |   |   | 105 |   |   |   |   | 110 |   |   |

| ATC | AAC | ACA | GGG | TTC | TAC | ATT | CGC | TCT | TAC | AGA | CGT | GTG | GAA | TAG |   | 801 |
|---|---|---|---|---|---|---|---|---|---|---|---|---|---|---|---|---|
| Ile | Asn | Thr | Gly | Phe | Tyr | Ile | Arg | Ser | Tyr | Arg | Arg | Val | Glu | * |   |   |
|   |   |   |   | 115 |   |   |   |   | 120 |   |   |   |   | 125 |   |   |

```
GTGATTAACT ATATCAACCG TAATGGAAAA TTCGTGAACC GAAATTTCAT TTTTGAGGAT        861

ACCACACCAA CTTGCGCTCA GATCCGTCAC GTTATATATT TCTATAATTT ACGCTTTAAT        921

AGGTGAATGT ACTATGAAGG CCTCTTTAGA AATTTATACC TCTTTTGATT ATAGTGGCAC        981

TATGATTATA TAGTGCGTGT GATTGCTAGA GAAAATTTCA GAAAACTTCC GTATCGTCTG       1041

CACTGACATT GCTCAAGCAC CAAAAAAGCA GTCTCCTGAT ATGTCACTTA AGATCAAGAA       1101

TAGATGTTTA GATGTAGCTA GTGTTTATCT GACAATAAAA GGACTCCTAA GGTACAAACG       1161

GCTGAGAGGC AAAGACTTTG AGGAATTTTG CTCAAGATTC TGTGATTCAG CCTTTACCAG       1221
```

-continued

CGACCTATCC ATGCACGAAG TACTCTCTA 1250

( 2 ) INFORMATION FOR SEQ ID NO:6:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Lys Phe Ser Phe Val Tyr Gly Leu Thr Gly Phe Leu Ala Ala Thr
 1           5                   10                  15

Ser Ser Ala Leu Pro Ser Glu Ile Leu Ser Thr Gly Tyr Glu Arg Ser
            20                  25                  30

Ala Leu Glu Lys Arg Gly Asp Gly Tyr Leu Ile Met Cys Lys Asn Cys
        35                  40                  45

Asp Pro Asn Thr Gly Ser Cys Asp Trp Lys Gln Asn Trp Asn Thr Cys
    50                  55                  60

Val Gly Ile Gly Ala Asn Val His Trp Met Val Thr Gly Gly Ser Thr
65                  70                  75                  80

Asp Gly Lys Gln Gly Cys Ala Thr Ile Trp Glu Gly Ser Gly Cys Val
                85                  90                  95

Gly Arg Ser Thr Thr Met Cys Cys Pro Ala Asn Thr Cys Cys Asn Ile
            100                 105                 110

Asn Thr Gly Phe Tyr Ile Arg Ser Tyr Arg Arg Val Glu
            115                 120                 125
```